(12) United States Patent
Congy et al.

(10) Patent No.: US 11,331,060 B2
(45) Date of Patent: May 17, 2022

(54) BITE BLOCK FOR CBCT IMAGING DEVICE

(71) Applicant: TROPHY, Marne la Vallee (FR)

(72) Inventors: Philippe Congy, Meaux (FR); Emilie Comte, Sucy en brie (FR)

( * ) Notice: Subject to any disclaimer, the term of this patent is extended or adjusted under 35 U.S.C. 154(b) by 129 days.

(21) Appl. No.: 15/542,259

(22) PCT Filed: Dec. 10, 2015

(86) PCT No.: PCT/IB2015/002544
§ 371 (c)(1),
(2) Date: Jul. 7, 2017

(87) PCT Pub. No.: WO2016/135526
PCT Pub. Date: Sep. 1, 2016

(65) Prior Publication Data
US 2017/0360384 A1    Dec. 21, 2017

Related U.S. Application Data

(60) Provisional application No. 62/121,873, filed on Feb. 27, 2015.

(51) Int. Cl.
*A61B 6/00* (2006.01)
*A61B 6/03* (2006.01)
(Continued)

(52) U.S. Cl.
CPC .............. *A61B 6/145* (2013.01); *A61B 6/032* (2013.01); *A61B 6/035* (2013.01); *A61B 6/04* (2013.01);
(Continued)

(58) Field of Classification Search
CPC ........... A61B 6/032; A61B 6/035; A61B 6/14; A61B 6/44; A61B 6/4429; A61B 6/4435;
(Continued)

(56) References Cited

U.S. PATENT DOCUMENTS

| | | | | |
|---|---|---|---|---|
| 6,118,842 | A * | 9/2000 | Arai ....................... | A61B 6/032 378/38 |
| 6,190,042 | B1 * | 2/2001 | Dove ..................... | A61B 6/145 378/167 |
| 6,243,439 | B1 * | 6/2001 | Arai ....................... | A61B 6/032 378/162 |
| 6,343,875 | B1 * | 2/2002 | Eppinger ............. | G03B 42/042 378/170 |
| 6,424,694 | B1 * | 7/2002 | Molteni ................... | A61B 6/04 378/168 |

(Continued)

FOREIGN PATENT DOCUMENTS

JP          2014-124287 A      7/2014
WO    WO 2014/037770 A1     3/2014

OTHER PUBLICATIONS

International Search Report dated May 12, 2016 for International Application No. PCT/IB2015/002544, 2 pages.
(Continued)

*Primary Examiner* — Allen C. Ho

(57) ABSTRACT

An extra-oral dental imaging apparatus can obtain a radiographic image of a portion of a head of a patient. Exemplary dental apparatus and/or method embodiments can position a subject for dental radiographic imaging by providing a bitable dental arch mounting apparatus to offset the anteroposterior plane of the dental imaging apparatus and the plane of symmetry of the dental arch mounting apparatus. In one embodiment, the offset can be provided by a tilted dental arch mounting apparatus (e.g., relative to the horizontal).

16 Claims, 15 Drawing Sheets

(51) Int. Cl.
*A61B 6/04* (2006.01)
*A61B 6/14* (2006.01)
*A61B 6/06* (2006.01)
*A61B 8/08* (2006.01)
*A61B 8/00* (2006.01)

(52) U.S. Cl.
CPC .......... *A61B 6/0407* (2013.01); *A61B 6/0421* (2013.01); *A61B 6/06* (2013.01); *A61B 6/14* (2013.01); *A61B 6/4085* (2013.01); *A61B 6/44* (2013.01); *A61B 6/4429* (2013.01); *A61B 6/4435* (2013.01); *A61B 6/4441* (2013.01); *A61B 6/501* (2013.01); *A61B 8/0875* (2013.01); *A61B 8/40* (2013.01)

(58) Field of Classification Search
CPC ......... A61B 6/4441; A61B 6/501; A61B 6/04; A61B 6/145; A61B 6/0407; A61B 6/0421; A61B 6/4447
USPC ..... 378/196, 197, 8–40, 168–170, 204, 205, 378/208
See application file for complete search history.

(56) References Cited

U.S. PATENT DOCUMENTS

| | | | | |
|---|---|---|---|---|
| 6,540,399 | B1* | 4/2003 | Eppinger | G03B 42/042 378/170 |
| 6,619,839 | B2* | 9/2003 | Yoshimura | A61B 6/0478 378/195 |
| 6,974,253 | B2* | 12/2005 | Ihalainen | A61B 6/14 378/168 |
| 7,033,075 | B2* | 4/2006 | Landis | A61B 6/145 378/168 |
| 7,036,985 | B2* | 5/2006 | Puente | A61B 6/14 378/170 |
| 7,090,395 | B2* | 8/2006 | Glazer | A61B 6/145 378/191 |
| 7,281,847 | B2* | 10/2007 | Kokkaliaris | A61B 6/145 348/E5.026 |
| 7,425,095 | B2* | 9/2008 | Schmulenson | G03B 42/042 378/170 |
| 7,497,619 | B2* | 3/2009 | Stoeckl | A61B 6/04 378/204 |
| 7,534,038 | B2* | 5/2009 | Rotondo | A61B 6/08 378/205 |
| 7,572,058 | B2* | 8/2009 | Pruss | A61B 6/04 378/208 |
| 7,695,191 | B1* | 4/2010 | Buchanan | A61B 6/14 378/170 |
| 7,871,199 | B2* | 1/2011 | Szommer | A61B 6/04 378/170 |
| 7,876,877 | B2* | 1/2011 | Stockl | A61B 6/14 378/208 |
| 7,929,661 | B2* | 4/2011 | Borghese | A61B 5/0064 378/37 |
| 8,016,483 | B2* | 9/2011 | Steward, Jr. | A61B 6/145 378/168 |
| 8,142,074 | B2* | 3/2012 | Schmulenson | G03B 42/042 378/170 |
| 8,177,428 | B2* | 5/2012 | Steck | A61B 6/145 378/168 |
| 8,290,119 | B2* | 10/2012 | Tancredi | A61B 6/14 378/197 |
| 8,396,186 | B2* | 3/2013 | Tomoe | A61B 6/14 378/39 |
| 8,503,603 | B2* | 8/2013 | Tancredi | A61B 6/0478 378/39 |
| 8,634,631 | B2* | 1/2014 | Kanerva | A61B 6/03 382/132 |
| 8,641,275 | B2* | 2/2014 | Fenske | A61B 6/145 378/168 |
| 8,750,450 | B2* | 6/2014 | Ulrici | A61B 6/14 378/38 |
| 8,817,944 | B2* | 8/2014 | Arai | A61B 6/06 378/11 |
| 8,855,262 | B2* | 10/2014 | Takemoto | A61B 6/02 378/197 |
| 8,861,679 | B2* | 10/2014 | Suuronen | A61B 6/00 378/98.5 |
| 8,876,375 | B2* | 11/2014 | Laude | A61B 6/4283 378/170 |
| 8,891,845 | B2* | 11/2014 | Ogawa | A61B 6/14 382/128 |
| 8,979,366 | B2* | 3/2015 | Tomoe | A61B 6/027 378/197 |
| 8,988,517 | B2* | 3/2015 | Mori | A61B 6/032 348/77 |
| 9,036,775 | B2* | 5/2015 | Yoshikawa | A61B 6/145 378/38 |
| 9,036,776 | B2* | 5/2015 | Sadakane | A61B 6/145 378/38 |
| 9,084,568 | B2* | 7/2015 | Katsumata | A61B 6/14 |
| 9,113,799 | B2* | 8/2015 | Katsumata | A61B 6/032 |
| 9,119,575 | B2* | 9/2015 | Sadakane | A61B 6/03 |
| 9,144,410 | B1* | 9/2015 | Chen | A61B 6/145 |
| 9,192,342 | B2* | 11/2015 | Roudergues | A61B 6/501 |
| 9,216,003 | B1* | 12/2015 | Chen | A61B 6/145 |
| 9,299,190 | B2* | 3/2016 | Koivisto | A61B 5/0064 |
| 9,314,215 | B2* | 4/2016 | Abramovich | A61B 6/4435 |
| 9,332,948 | B2* | 5/2016 | Thoma | A61B 6/032 |
| 9,339,252 | B2* | 5/2016 | Sugihara | A61B 6/032 |
| 9,351,701 | B2* | 5/2016 | Yamakawa | A61B 6/025 |
| 9,357,971 | B2* | 6/2016 | Yoshikawa | A61B 6/032 |
| 9,384,580 | B2* | 7/2016 | Keating | G06K 9/00362 |
| 9,389,320 | B2* | 7/2016 | Ogawa | A61B 6/14 |
| 9,408,579 | B2* | 8/2016 | Yamakawa | A61B 6/14 |
| 9,414,791 | B2* | 8/2016 | Jun | A61B 6/14 |
| 9,439,609 | B2* | 9/2016 | Bianconi | A61B 6/14 |
| 9,480,453 | B2* | 11/2016 | Yamanaka | A61B 6/035 |
| 9,498,170 | B2* | 11/2016 | Schwarzbach | A61B 6/145 |
| 9,504,434 | B2* | 11/2016 | Bianconi | A61B 6/04 |
| 9,510,795 | B2* | 12/2016 | Takemoto | A61B 6/14 |
| 9,668,705 | B2* | 6/2017 | Yamakawa | A61B 6/14 |
| 9,724,051 | B2* | 8/2017 | Yoshimura | A61B 6/0478 |
| 9,743,893 | B2* | 8/2017 | Inglese | A61B 6/14 |
| 9,750,470 | B2* | 9/2017 | Jun | A61B 6/145 |
| 9,888,891 | B2* | 2/2018 | Suuronen | A61B 6/4452 |
| 9,901,313 | B2* | 2/2018 | Schmulenson | A61B 6/145 |
| 9,936,926 | B2* | 4/2018 | Eronen | A61B 6/4035 |
| 9,962,131 | B2* | 5/2018 | Yoshikawa | A61B 6/4035 |
| 9,974,493 | B2* | 5/2018 | Kim | A61B 6/027 |
| 9,993,212 | B2* | 6/2018 | Takemoto | A61B 6/027 |
| 10,004,468 | B2* | 6/2018 | Choi | A61B 6/14 |
| 10,076,291 | B2* | 9/2018 | Arai | A61B 6/06 |
| 10,172,571 | B2* | 1/2019 | Park | A61B 6/02 |
| 10,204,443 | B2* | 2/2019 | Fleer | G06T 15/08 |
| 10,231,681 | B2* | 3/2019 | Bruno | A61B 6/14 |
| 10,251,736 | B2* | 4/2019 | Nakai | A61C 19/041 |
| 10,265,033 | B2* | 4/2019 | Lim | A61B 6/035 |
| 10,307,119 | B2* | 6/2019 | Lim | A61B 6/4417 |
| 10,617,373 | B2* | 4/2020 | Ahn | A61B 6/03 |
| 10,939,882 | B2* | 3/2021 | Alric | A61B 6/032 |
| 2002/0122537 | A1 | 9/2002 | Yoshimura | |
| 2011/0026669 | A1 | 2/2011 | Tancredi et al. | |
| 2015/0297158 | A1* | 10/2015 | Bothorel | A61B 6/06 378/20 |

OTHER PUBLICATIONS

International Preliminary Report on Patentability dated Aug. 29, 2017 from International Application No. PCT/IB2015/002544; 9 pages.

* cited by examiner

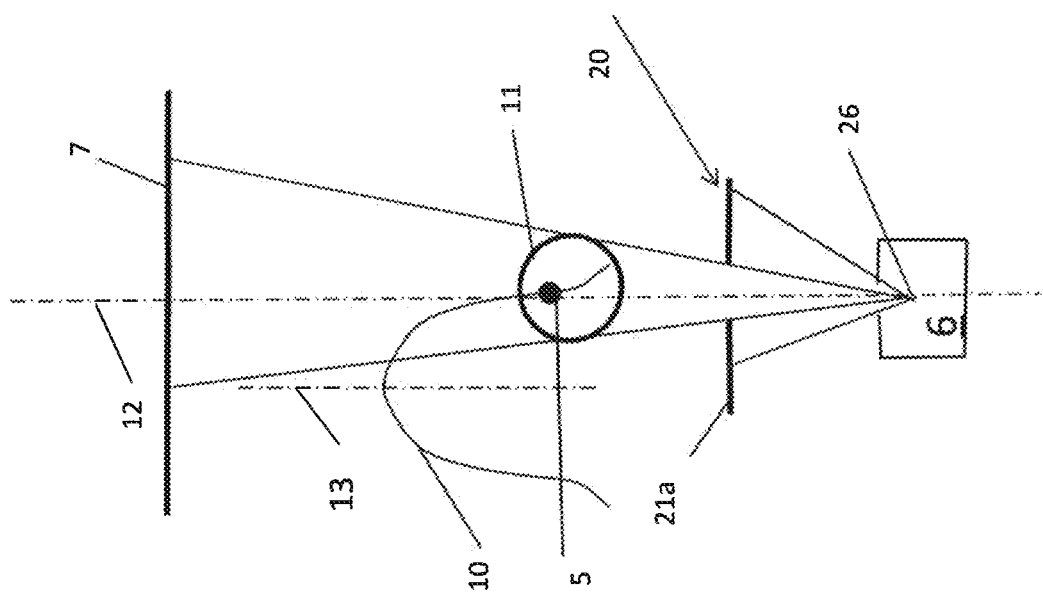

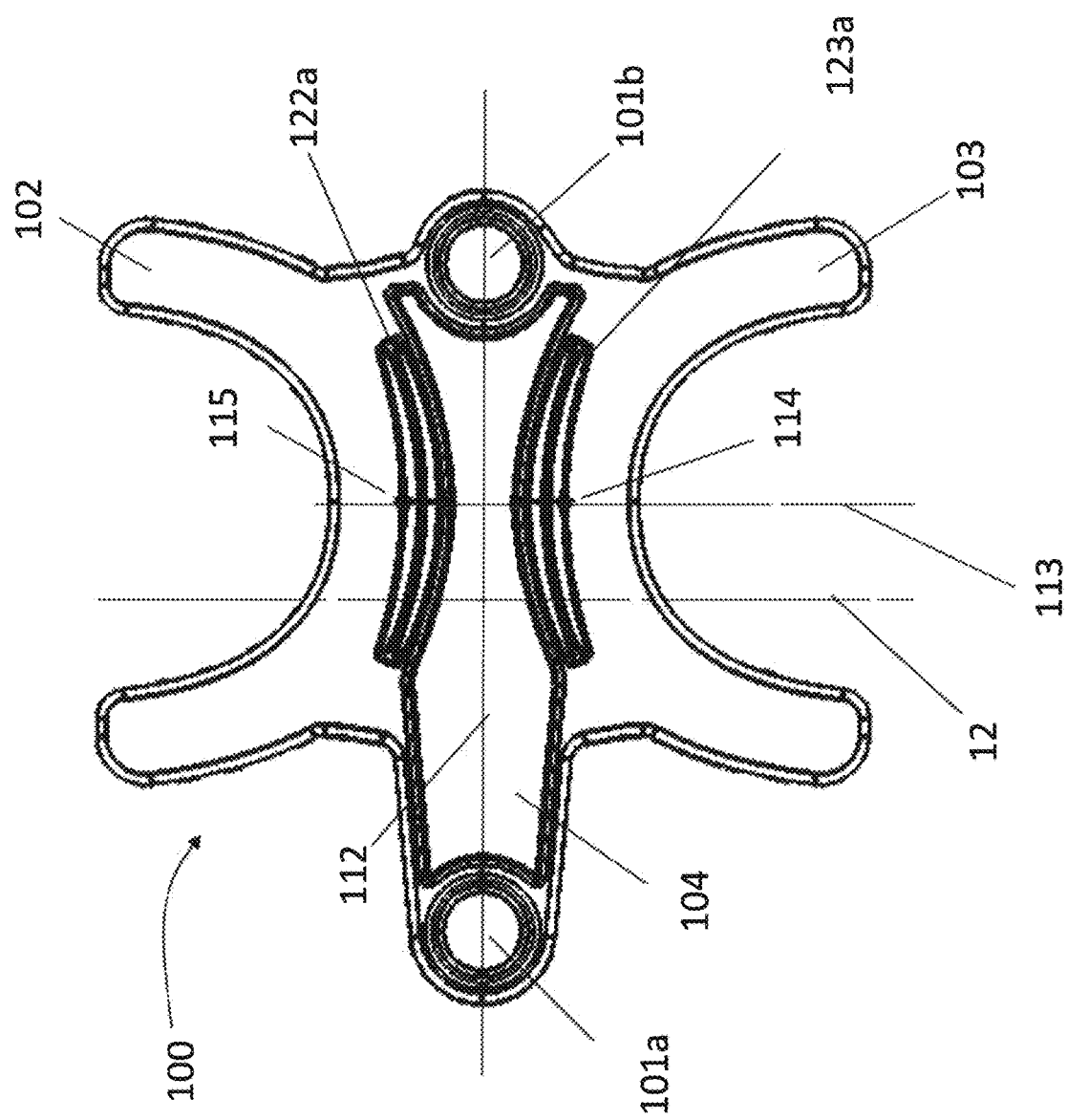

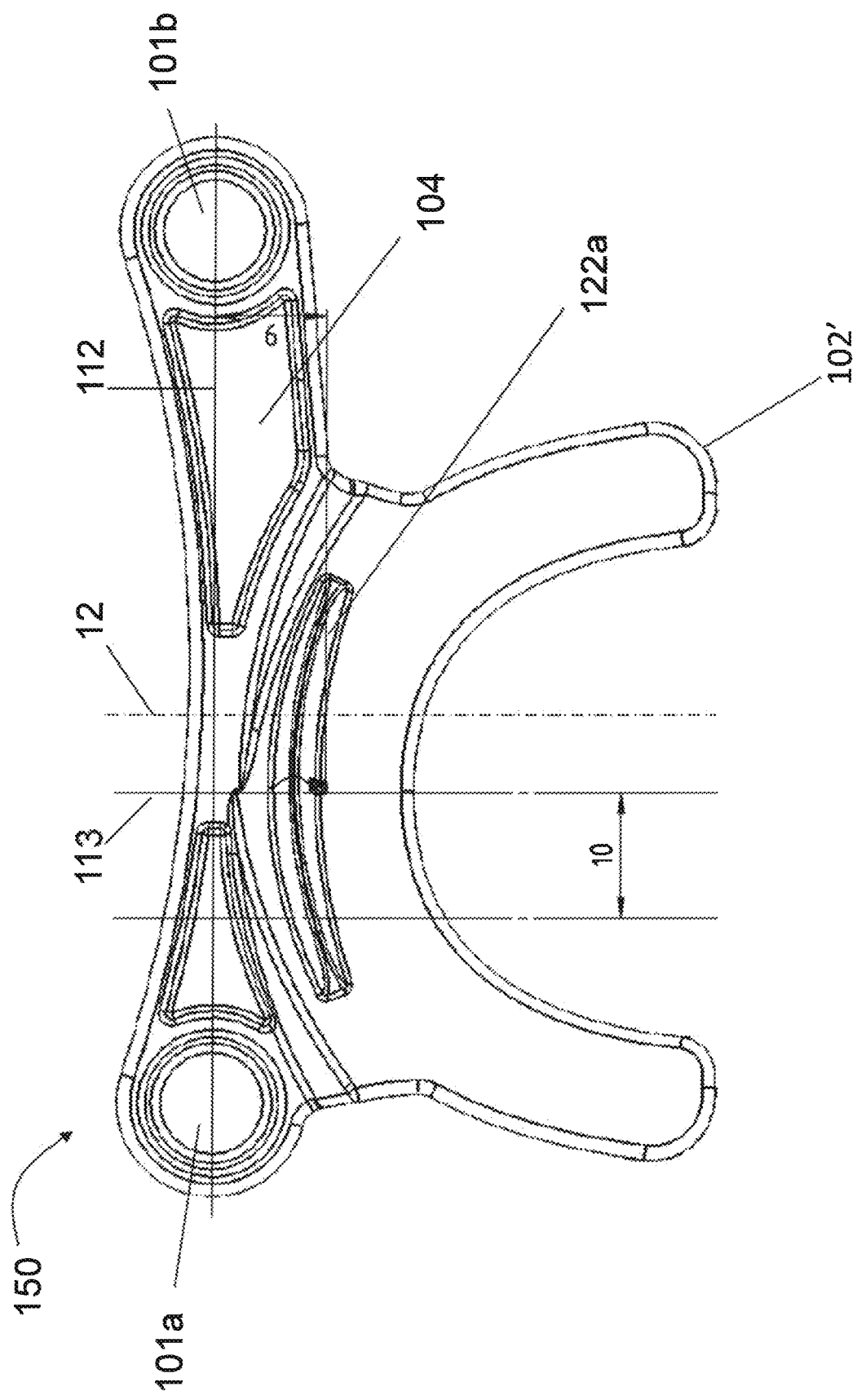

BITE BLOCK FOR CBCT IMAGING DEVICE

CROSS REFERENCE TO RELATED APPLICATIONS

This application claims the benefit of and is a U.S. National Phase filing of PCT Application PCT/IB2015/002544 filed Dec. 10, 2015 entitled "BITE BLOCK FOR CBCT IMAGING DEVICE", in the name of Philippe Congy et al, which claims benefit of U.S. Provisional application U.S. Ser. No. 62/121,873, provisionally filed on Feb. 27, 2015, entitled "BITE BLOCK FOR CBCT IMAGING DEVICE", in the name of Philippe Congy, all of which are incorporated herein in their entirety.

FIELD OF THE INVENTION

The invention relates generally to the field of medical x-ray imaging, and more particularly, dental imaging apparatus and/or methods for dental X-ray Computerized Tomography (CT) or Cone Beam Computerized Tomography (CBCT) imaging.

BACKGROUND

A computerized tomography (CT) or cone beam CT (CBCT) imaging apparatus can include a vertical column that can support a movable or rotating imaging ensemble or gantry, for example, using a horizontal mount. The gantry can support an x-ray source and a sensor opposite to each other and configured to rotate about a rotary axis located between the x-ray source and the sensor. An object or the patient positioned on a patient's positioning unit including a bite block can be located between an x-ray source and sensor.

The CT or CBCT imaging apparatus operates by acquiring multiple 2D images with the gantry rotating about the patient or imaging area (e.g., a fixed rotary axis relative to the patient who is being imaged). CT and CBCT imaging allow the reconstruction of 3D or volume images of anatomical structures of the patient. The resulting volume images are acknowledged to be of particular value for obtaining useful information for assisting diagnosis and treatment.

During a CBCT scan, the x-ray source and sensor supported by the gantry can rotate about a fixed rotary axis in an angular range of at least 180° while the x-ray source emits the x-ray beam. A region to be three dimensionally reconstructed is constantly (e.g., pulsed) irradiated by the x-ray beam due to a precise collimation of the x-ray beam by a collimator located in front of the x-ray source. The x-ray beam can be emitted during the whole angular range of the scan (or CBCT exposure). The patient positioned on the patient's positioning unit and the gantry supporting the x-ray source and sensor must be in a very precise relationship such that the region constantly irradiated during the scan coincides or corresponds with the region of interest of the patient to be reconstructed.

In the disclosure of prior art U.S. Pat. No. 6,619,839, a gantry is movable in two dimensions relative to the mount so that the rotary axis is positioned at the vertical position of the region of interest of the patient before the beginning of the scan. During the scan, the rotary axis is fixed and the gantry rotates about the rotary axis. The collimator in front of a source shapes the beam in such a way that the center of the beam crosses the vertical position of the rotary axis. The reconstructed image is a vertical cylinder centered on the rotary axis. Then, a precise positioning of the rotary axis relative to the patient allows the scan and reconstruction of the desired region of interest, but necessitates the integration in the mount of a rotary axis displacement means including at least two motors for the displacement of the rotary axis in two dimensions crossing the direction of the rotary axis. Thus, U.S. Pat. No. 6,619,839 results in a complicated, bulky and expensive apparatus.

In the disclosure of another prior art published patent application WO2014/037770, a gantry of a CBCT device can be displaced in only one single direction, for example the antero-posterior direction (namely the front-to-back direction relative to the patient), or even cannot be displaced at all. The region of interest is then generally not located at the vertical position of the fixed rotary axis. The x-ray beam is dynamically collimated by the collimator located in front of the source so that the beam passes through the region of interest at each angular position of the gantry during the scan. Nevertheless, the sensor, which is generally the most expensive element of the CBCT device, is necessarily of a limited size. When the region of interest, for example a third molar or a condyle, is located at a position remote from the vertical position of the rotary axis, the center of the beam is highly offset relative to the vertical position of the rotary axis. As the sensor is fixed and centered on the axis that links the source and the rotary axis, the beam does not impinge the sensor. The drawback of the application WO2014/037770 disclosure is that condyles and third molars can then not be 3D imaged.

In the disclosure of yet another prior art U.S. Pat. No. 8,503,603, both the collimation of the x-ray beam and the position of the sensor are dynamically monitored during the scan so that the beam radiates the region of interest and the sensor captures the beam at each angular position of the gantry during the scan. The elements of the patient's jaw remote from the rotary axis can then be imaged. Nevertheless, the sliding mechanism that allows the displacement of the sensor is complicated and expensive and the displacement of the sensor at each angular position may be difficult to monitor.

In an imaging apparatus that does not allow displacement of the rotary axis relative to the patient's positioning unit or in which a displacement of the rotary axis along one single direction is allowed, it may be relevant to change the position of the patient relative to the rotary axis before the scan. A motorized patient positioning means is disclosed in prior art patent U.S. Pat. No. 6,118,842. Two motors make possible the displacement of the bite block in the lateral (X) and antero-posterior (Y) directions. Again, the use of a motorized bite block increases the manufacturing cost of the machine.

There is still a need for a CT or CBCT device provided with capabilities to change the position of the patient before the scan, in order to allow the imaging of any part of the patient's jaw such as the third molars and/or the condyles, when the rotary axis of the CBCT device cannot be displaced in two directions crossing the direction of the rotary axis.

SUMMARY

An aspect of this application is to advance the art of medical digital radiography, particularly for dental applications.

Another aspect of this application is to address, in whole or in part, at least the foregoing and other deficiencies in the related art.

It is another aspect of this application to provide, in whole or in part, at least the advantages described herein.

An advantage offered by apparatus and/or method embodiments of the application relates to improved imaging of teeth, jaw or head features surfaces at a lower cost over conventional imaging methods.

An advantage offered by apparatus and/or method embodiments of the application relates to proper positioning in an imaging area of a dental imaging apparatus.

An advantage offered by apparatus and/or method embodiments of the application relates to repeatable, consistent, and/or accurate positioning in an imaging area of a dental imaging apparatus.

An advantage offered by apparatus and/or method embodiments of the application relates to performing partial CT or CBCT imaging in a simplified and/or less costly configurations.

An advantage offered by apparatus and/or method embodiments of the application relates to correct positioning for dental X-ray CT or CBCT imaging.

According to one aspect of the disclosure, there is provided a method of positioning a subject for dental radiographic imaging, executed at least in part on data processing hardware, that can include providing a bitable bite block including opposing surfaces in a patient support structure to provide a prescribed spatial relationship, where the prescribed spatial relationship offsets the antero-posterior plane of the dental imaging apparatus and the plane of symmetry of a dental arch mounting apparatus.

According to one aspect of the disclosure, there is provided a dental imaging apparatus for obtaining a radiographic image of an object that can include a movable mount comprising at least one of a radiation source and a digital imaging sensor; an actuator that is energizable to move the movable mount in a scan pattern about an imaging area; a computer in signal communication with the digital imaging sensor and configured to acquire one or more of two-dimensional images of the digital imaging sensor positioned relative to the radiation source for the scan pattern; and a patient support structure to provide a spatial relationship to the scan pattern, where the spatial relationship offsets the antero-posterior plane and the plane of symmetry of the dental arch.

These objects are given only by way of illustrative example, and such objects may be exemplary of one or more embodiments of the invention. Other desirable objectives and advantages inherently achieved by the may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other. Some exaggeration may be necessary in order to emphasize basic structural relationships or principles of operation. Some conventional components that would be needed for implementation of the described embodiments, such as support components used for providing power, for packaging, and for mounting and protecting system optics, for example, are not shown in the drawings in order to simplify description.

FIG. 5c is diagram that shows an exemplary CBCT imaging process for a region of interest that is far remote from the vertical location of the rotary axis with a patient positioning unit according to certain exemplary embodiments of the application.

FIG. 6a-6c are diagrams that show an exemplary bite block embodiment according to the application.

FIG. 9a-9c are diagrams that show another exemplary bite block embodiment with an offset and tilted bite plate according to the application.

DESCRIPTION OF EXEMPLARY EMBODIMENTS

Figure 1:
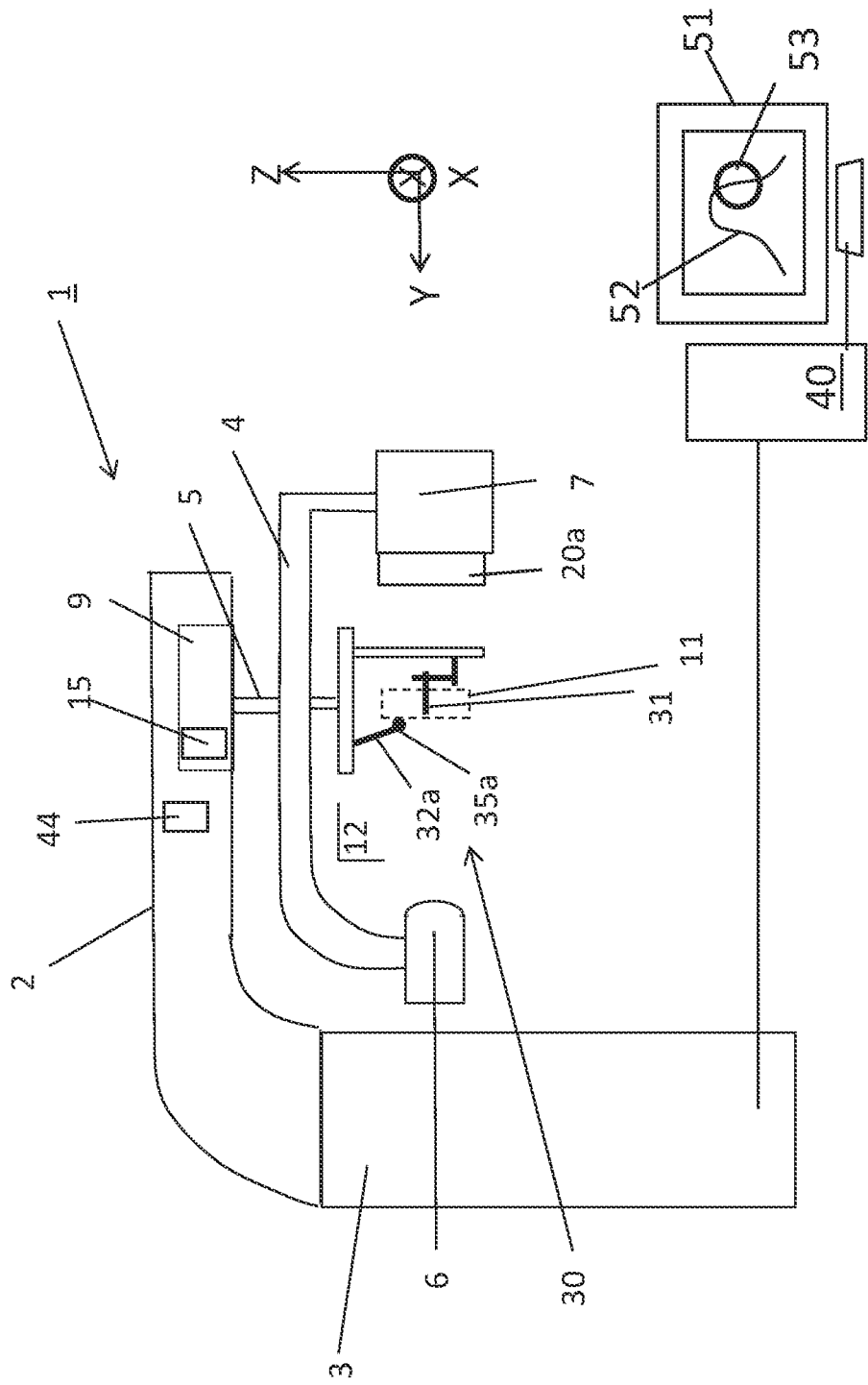
FIG. 1 is a diagram that shows a functional view of an exemplary related art CBCT dental imaging device including a patient positioning unit.

The following is a description of exemplary embodiments, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal. The term "actuable" has its conventional meaning, relating to a device or component that is capable of effecting an action in response to a stimulus, such as in response to an electrical signal, for example.

Apparatus and/or method embodiments according to the application aim at facilitating a repeatable, accurate and/or controllable partial CT imaging. Apparatus and/or method embodiments according to the application provide CT or Cone Beam CT dental imaging.

FIG. 1 is a diagram that shows a simplified side view of an exemplary prior art CBCT dental imaging device including a patient positioning unit. As shown in FIG. 1, a CBCT imaging device 1 can include a horizontal mount 2 supported by a vertical column 3. The vertical position of the horizontal mount 2 can be adjustable relative to the vertical column 3 so that the horizontal mount 2 can adjust to the patient's height. A gantry 4 can support an x-ray source 6 and an imaging sensor 7 to revolve around an imaging area of the CBCT device 1. The gantry 4 can be mounted to or coupled to the horizontal mount 2. In one example, the gantry 4 can be mounted to the horizontal mount 2 via an axis 5 and can rotate about the axis 5. In an alternative configuration, a rotating displacement unit 9 can be incorporated on the mount 2 and include a motor 15 for the displacement of the axis 5 along at least the antero-posterior direction (e.g., Y direction) relative to the patient. An exemplary patient positioning unit 30 can include a bite block 31 and two temporal holders 32a and 32b equipped with temporal contacts 35a and 35b. For example, the patient positioning unit 30 is supported by the mount 2. A collimator 20, which can be a blade collimator or a shutter collimator, can be positioned in front of the x-ray source 6 to shape and orient an x-ray beam originating from the x-ray source 6 to scan a region of interest 11. Preferably, after passing through the region of interest 11, the x-ray beam can impinge the imaging sensor 7. Optionally, a second collimator 20a can be placed near or in front of the imaging sensor 7.

A control logic processor 40, that may or may not be integral or co-located with the CBCT imaging device 1, can control movements of the gantry 4 (e.g., rotation of the gantry 4), the aperture of the collimator 20 and/or optionally the displacement of the axis 5 (e.g., for positioning the axis 5) before the scan. One or more sensor elements 44, in signal communication with control logic processor 40, can sense the rotational position of rotatable gantry 4 and, optionally, also sense the relative positions of axis of rotation 5 in the Y direction. The control logic processor 40 can be connected to a screen 51 that may or may not be integral with the CBCT imaging device 1.

The screen 51 can display a model 52 of the dental arch of the patient and a target 53 that is changeable in size and in position relative to the model 52 of the dental arch via a Graphical User Interface (GUI) or the like. The target 53 can be a virtual representation of the region (e.g., region of interest 11) to be reconstructed. Alternatively, the target 53 can be in the form of a highlighting of a part of the virtual model or representation of the dental arch (e.g., 2D, 3D or simplified) displayed on the screen 51 corresponding to the part of the physical dental arch that has been selected to be irradiated. Information relative to size and/or position of the target 53 relative to the virtual model of the dental arch or jaw can be sent to the control logic processor 40. The control logic processor 40 can then position the axis 5 of the gantry 4 at a calculated position relative to the patient corresponding to the position of (e.g., the center) of the virtual target and can actuate the collimator 20 in order to shape and direct the x-ray beam for the irradiation of the part of the physical dental arch corresponding to the position of the virtual target at any angular position of the gantry 4.

Figure 2:
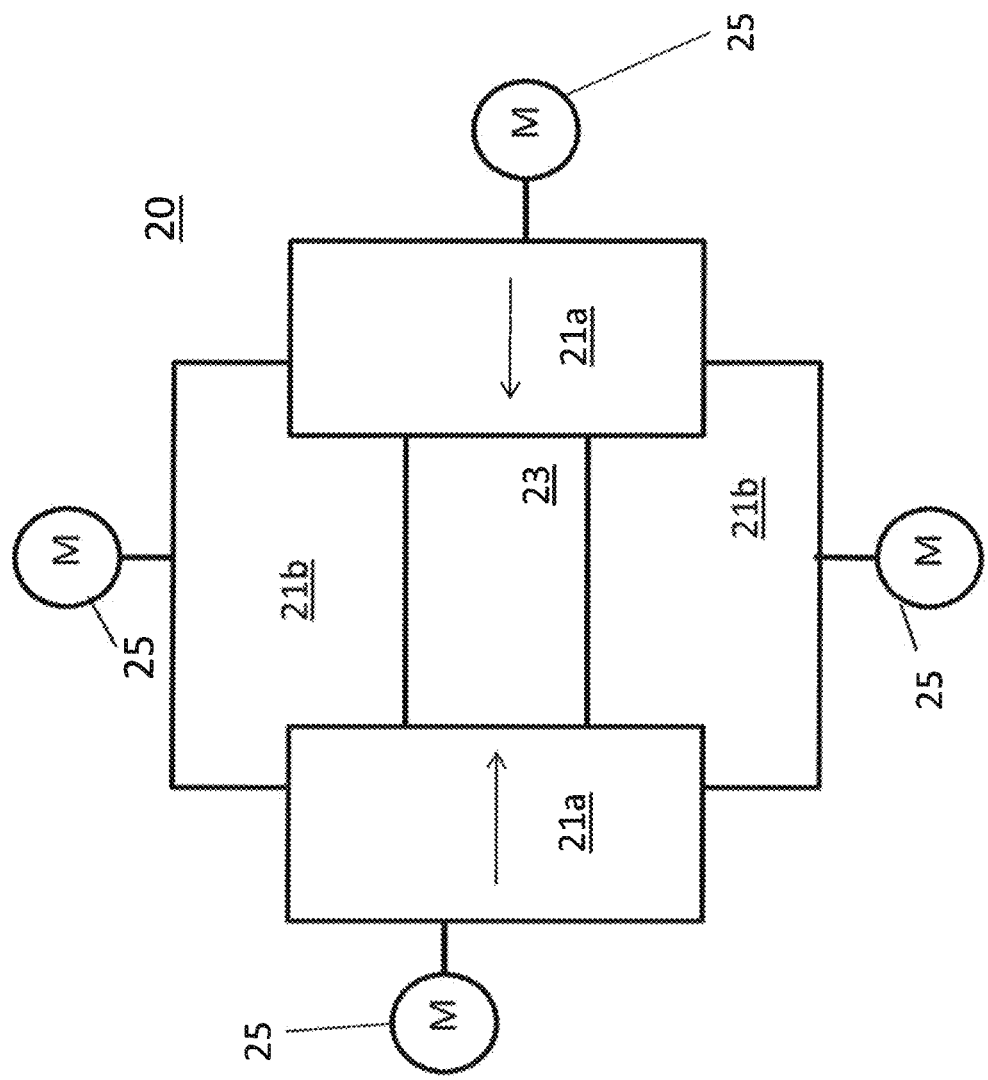
FIG. 2 is a diagram that shows an exemplary related art collimator including four blades.

Thus, the collimator 20 can operate to center an x-ray beam 23 at each angular position of the x-ray source 6 and imaging sensor 7 (or gantry 4). FIG. 2 is a diagram that shows components that can form and/or control exemplary collimator 20. As shown in FIG. 2, an exemplary collimator 20 can shape an x-ray beam 23 that is rectangular in cross section. In FIG. 2, the collimator 20 is a blade collimator, provided with paired blades 21a, 21b that are appropriately positioned by motors 25, that can be controlled by the control logic processor 40. In conventional practice, the blades 21a, 21b are positioned in such a manner that the position and width of the x-ray beam 23 conforms to the position and/or size of the virtual target 53. As known to one skilled in the art, other types of collimators may be used in alternate x-ray beam shaping configurations, such as those providing circular, wedge and elliptical apertures. In alternate configurations, a collimator can asymmetrically drive the blades or form an asymmetric shaped x-ray beam. In alternate configurations, a shutter collimator with a cam mechanism actuating the shutters can also be used.

Figure 3:
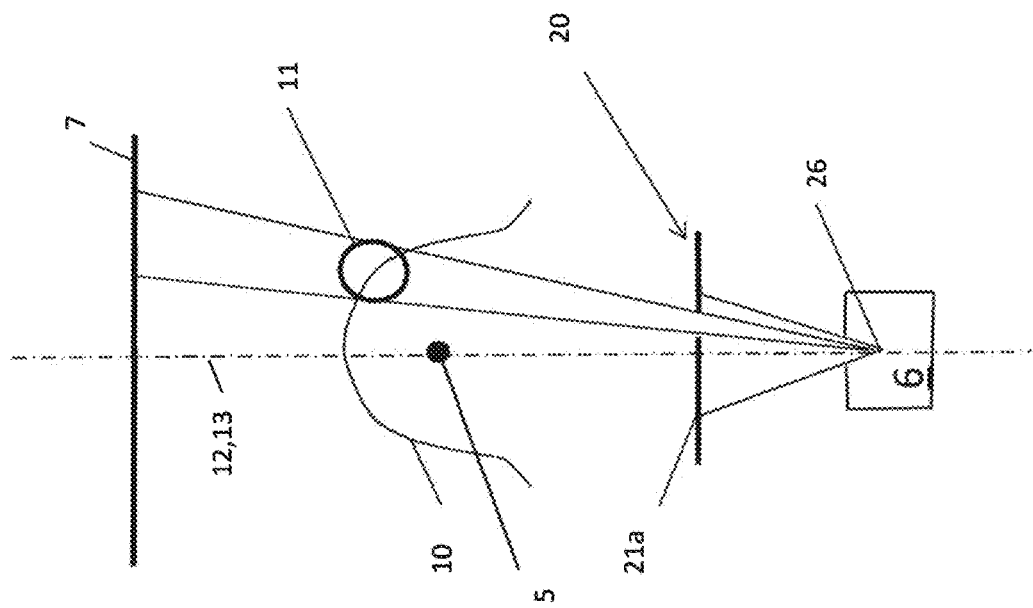
FIG. 3 is a diagram that shows a top view illustrating exemplary CBCT imaging of a region of interest located away from the vertical position of the rotary axis according to the related art.

With the collimator 20 actuated accordingly, the x-ray beam 23 originating from a focal spot 26 of the x-ray source 6 radiates the region of interest 11 of a dental arch 10 and then impinges the sensor 7 as shown in FIG. 3. The antero-posterior plane 12 of the CBCT imaging device 1 can be defined as the vertical plane oriented in the front-to-rear direction of the patient when the patient is positioned on the patient positioning unit 30 and containing the rotary axis 5. As shown in FIG. 3, the region of interest 11 is offset relative to the antero-posterior plane 12 of the CBCT imaging device 1. In the situation of FIG. 3, the patient positioning unit 30 and especially the bite block 31 are centered relative to the antero-posterior plane 12 the CBCT imaging device 1. When the patient is thus positioned, a plane of symmetry 13 of the dental arch 10 coincides with the antero-posterior plane 12 of the CBCT imaging device 1. Thus, FIG. 3 is a diagram that shows a top view illustrating exemplary prior art CBCT imaging of a region of interest 11 located away from the vertical position of the rotary axis 5.

Figure 4B:
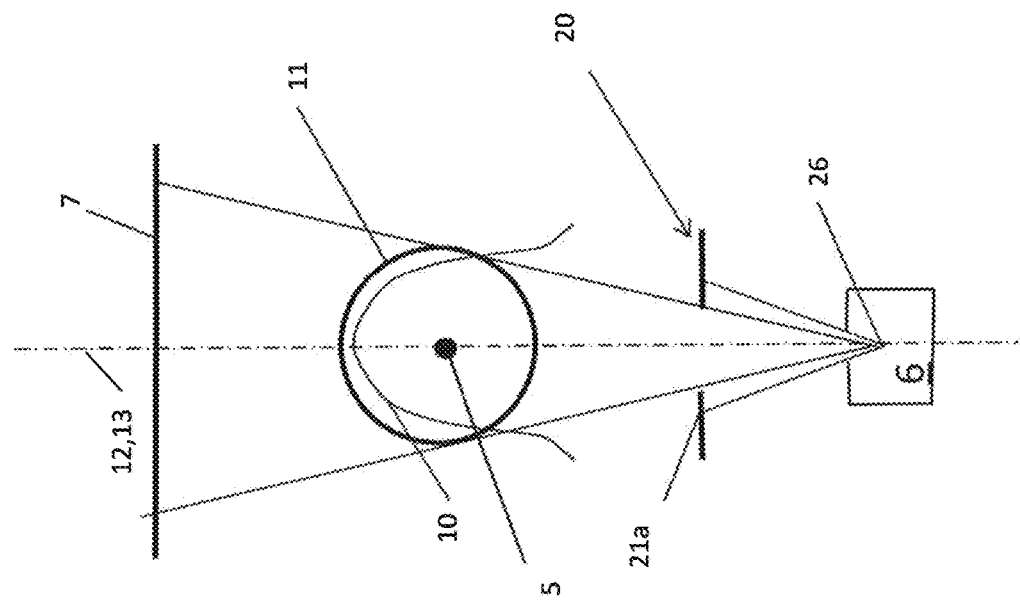
FIGS. 4a and 4b are diagrams that show exemplary related art CBCT imaging process of a region of interest centered on the vertical position of the rotary axis.
Figure 4A:
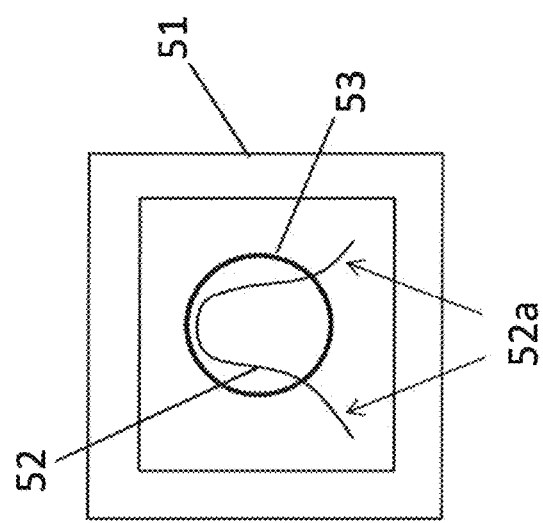

The maximum size of a region of interest 11 that it is possible to reconstruct is limited by the size of the imaging sensor 7 according to the prior art. As the price of the imaging sensor 7, and consequently the price of the CBCT imaging device 1, is highly impacted by the size of the imaging sensor 7, it may not be possible to cost-effectively image the whole dental arch with a CBCT imaging device 1. FIGS. 4a and 4b illustrate the case where the irradiation of the patient's jaw has the largest field of view of the CBCT imaging device 1. FIGS. 4a and 4b illustrate the case where the irradiation of the patient's jaw is at the particular angular position of the gantry 4 where the plane containing the focal spot 26 of the x-ray beam 23 is in the antero-posterior plane 12. As shown in FIGS. 4a-4b, the active surface of the imaging sensor 7 is fully impinged by the x-ray beam 23. Still, in FIGS. 4a-4b, one or both of the extremities 52a of the dental arch are not radiated, and consequently cannot be reconstructed. If the extremities 52a (e.g., third molars and/or condyles) were irradiated in FIGS. 4a-4b, the extremities 52a of the x-ray beam 23 would impinge outside of or beyond the active surface of the imaging sensor 7.

Figure 5B:
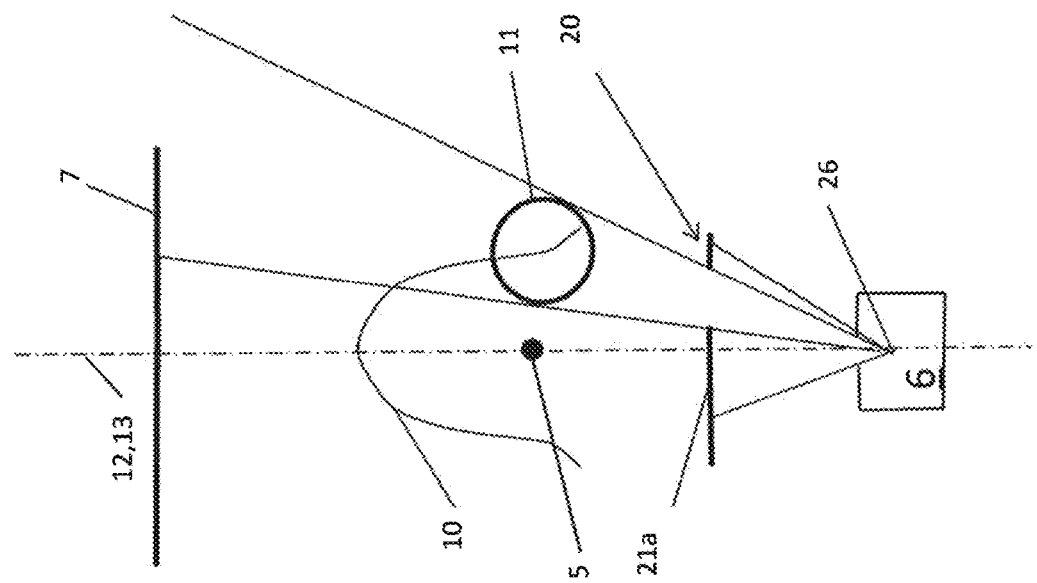
FIG. 5a-5b are diagrams that show limitations of the related art CBCT imaging process and/or patient positioning unit when imaging a region of interest that is far remote from the vertical location of the rotary axis.
Figure 5A:
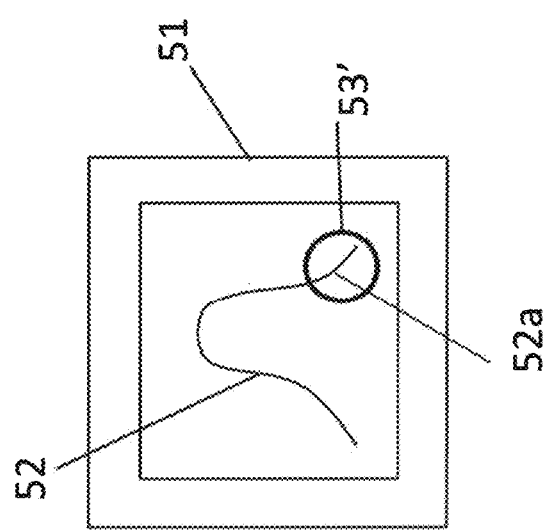

FIG. 5a-5b are diagrams that show limitations of the prior art CBCT imaging process and patient positioning unit 30 to image a region of interest 11 that is far remote from the vertical location of the rotary axis 5. As shown in FIG. 5a, the selection of a small field of view 53' centered on a third molar or on a condyle as sketched for the same angular position of the gantry 4 of FIG. 4b, would lead to a focal point 26 of the x-ray beam 23 at least partially out of the active surface area of the imaging sensor 7 in a case where the plane of symmetry 13 of the dental arch coincides with the antero-posterior plane 12 of the CBCT imaging device 1 (see FIG. 5b).

Apparatus and/or method embodiments according to the application can focus portions or the entirety of the x-ray beam on the active area of the sensor while radiating a region of interest corresponding to extremities 52a of the dental arch. One solution to focus the entirety of the beam on the active area of the sensor while radiating a region of interest centered on extremities 52a of the dental arch (e.g., a third molar or a condyle) according to apparatus and/or method embodiments of the application is to offset laterally the patient as represented on FIG. 5c. Then the plane of symmetry of the dental arch 13 does not coincide with the antero posterior plane 12 of a CBCT device. The region of interest 11 (e.g., corresponding to extremities of the dental arch) can then be positioned closer to the rotary axis 5 and the x-ray beam can radiate the region of interest 11 and still impinge the active surface of the sensor 7.

Figure 6B:
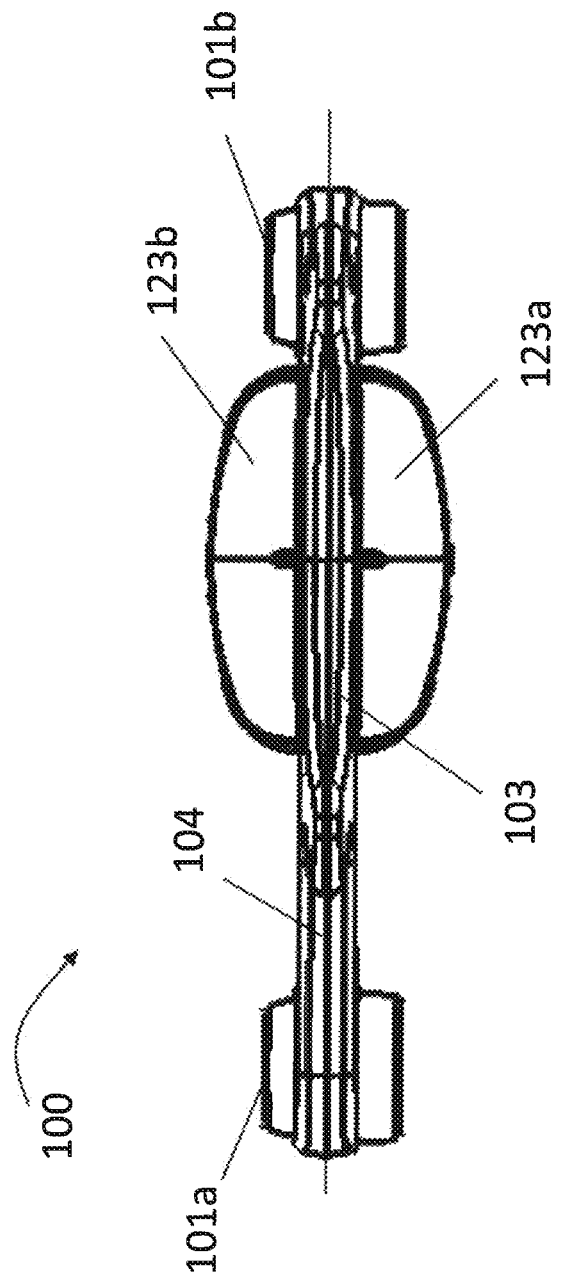
Figure 6C:
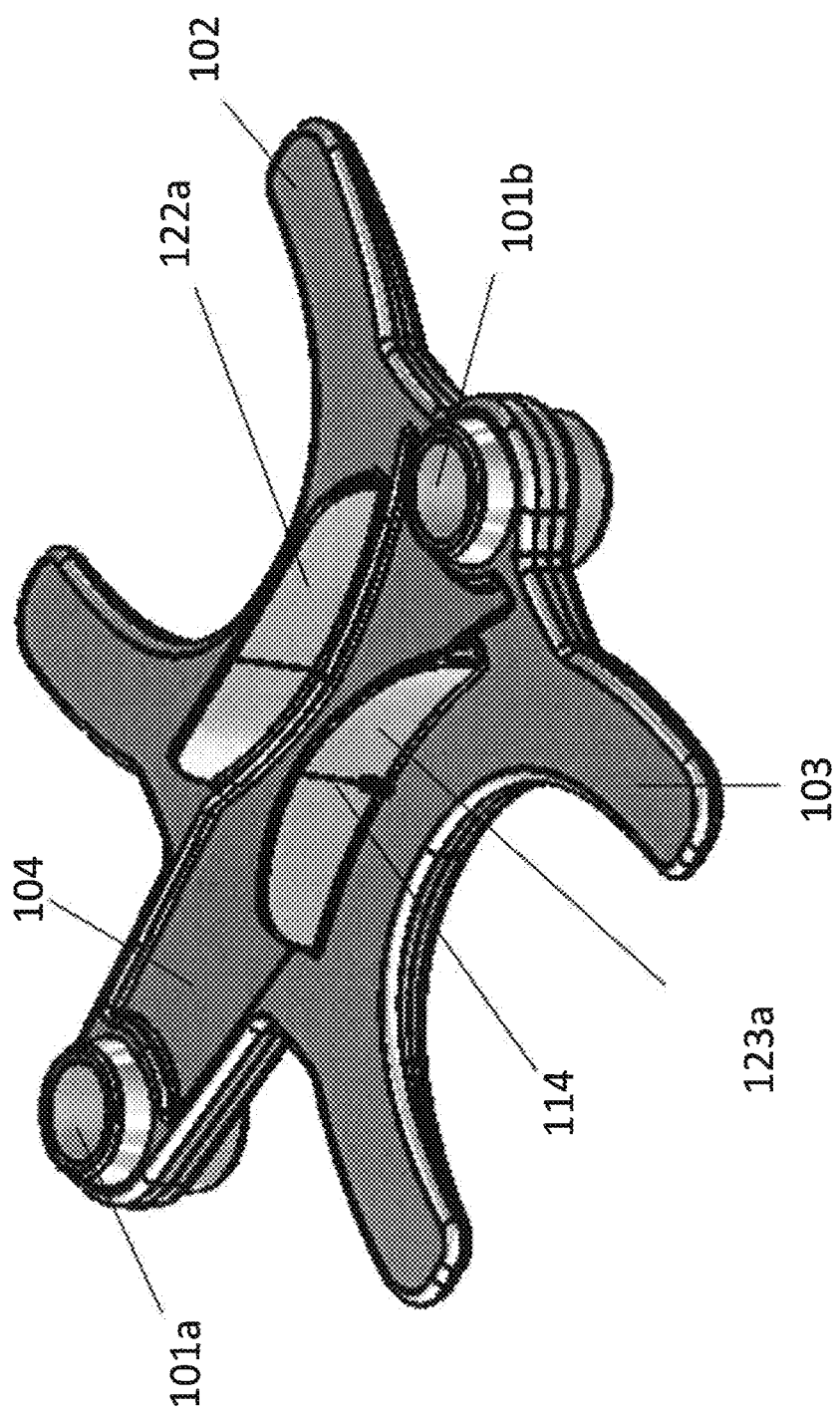

Imaging of patient features offset from the antero-posterior plane 12 of the CBCT device can be achieved by the use of an exemplary bite block embodiment as shown in FIGS. 6a-6c. An exemplary bite block embodiment 100 according to the application can include a planar element 104 with two protrusions extending on both sides of the planar element 104. The protrusions are bored so that a tapered hole 101a and 101b extends from the top face to the bottom face of each protrusion. In one embodiment, the exemplary bite block 100 can made of one single piece. The bite block 100 can then be positioned relative to the CBCT device 1 by respectively inserting two shafts 33a and 33b fixed on or coupled to a patient positioning unit 130 (or a patient support structure) inside the holes 101a and 101b of the bite block 100. The two shafts 33a and 33b (e.g., see FIG. 8) can be positioned symmetrically relative to the antero-posterior plane 12 of the CBCT imaging device 1. The plane 12 can intersect orthogonally a line 112 joining the centers of both holes 101a and 101b. The plane 12 can be at a position equidistant from the centers of both holes 101a and 101b when the bite block 100 is positioned on the shafts 33a and 33b. Two bite plates 102 and 103 can be linked to the planar element 104 in one embodiment on opposite sides (e.g., symmetrically) relative to the line 112 linking both holes 101a and 101b, respectively on opposing protrusions. A common plane of symmetry 113 of both bite plates 102 and 103 can be parallel to the axis 12 of the CBCT imaging device 1. The common plane of symmetry 113 of both bite plates 102 and 103 can be offset relative to the plane 12.

In certain exemplary embodiments, the distance between the plane of symmetry 113 of the bite plates and the antero posterior plane 12 of the CBCT imaging device 1 can be approximately 10 millimeters. The distance between the plane of symmetry 113 of the bite plates and the antero posterior plane 12 of the CBCT imaging device 1 can also more generally be in a 3-20 millimeters range. Preferably, the distance is in the range 8-12 millimeters, but the distance can also be in the range 5-10 millimeters. As shown in FIGS. 6a-6c, both bite plates can have shapes corresponding to the dental arch (e.g., horseshoe-shaped, u-shaped) and consequently fit conveniently the shape of both dental arches that contact the upper and the lower surfaces of one bite plate. An upper flange 122a and a lower flange 122b can be positioned on both sides of the bite plate 102 and serve as an abutment for the incisors to precisely position the dental arch on the bite plate 102. Upper flange 123a and a lower flange 123b can be positioned symmetrically on both sides of the bite plate 123. Physical indices 114 and 115 (e.g. visible) are provided respectively on upper flanges 123a and 122a to be inserted between the upper incisors and can further improve the positioning of teeth on the bite plate 100. Although a single indice 114 and 115 is shown for respective bite plate 102 and 103, addition indices can be utilized (e.g., for positioning) by embodiments of the application.

As shown in FIGS. 6a-6c, exemplary bite block 100 presents various advantages that if a right third molar or a right condyle has to be imaged, the bite block 100 is positioned on the shafts 33a and 33b of the patient positioning unit 30 (FIG. 1) such that the shafts 33a penetrates the hole 101a. Then the bite block 100 is positioned such that the relevant bite plate 102 faces the patient. The plane of symmetry 113 of the bite plate 102 is offset on the left of the antero posterior plane 12 of the CBCT imaging device 1. The positional of the right third molar or condyle of the patient biting the bite plate 102 is then displaced toward the antero posterior plane 12 compared to a standard/conventional bite block. If a left third molar or condyle has to be imaged, the bite block 100 is reversed on the shafts 33a and 33b such that the shaft 33a penetrates the hole 101b and the relevant bite plate 103 faces the patient. Then the plane of symmetry 113 of the bite plate 103 is offset on the right side of the antero posterior plane 12 of the CBCT imaging device 1. The positional of the left third molar or condyle of the patient biting the bite plate 103 is then displaced toward the antero posterior plane 12, compared to a standard bite block. In both cases, the region of interest 11 is brought closer to the rotary axis 5 because of the offset bite plate 102 or 103. In certain exemplary embodiments, it is possible to radiate the right or left third molar or condyle while limiting the angle between the center of the x-ray beam 23 and the antero posterior plane 12 of the CBCT imaging device 1 so that the x-ray beam 23 as a whole impinges the active surface area of the imaging sensor 12.

Though two offset bite plates 102 and 103 are linked to the planar element 104, an embodiment in which one single bite plate is provided can also be contemplated without departing from the scope of the invention. In that case, the user can change from a left offset to a right offset bite block 100 simply by reversing upside down the bite block 100. In that case, the holes 101a and 101b must not be tapered but need to be of cylindrical shape so that it is possible to penetrate the shafts 33a and 33b in either direction. A set of two bite blocks can also be contemplated, a first one being provided with a left offset bite plate 102 and the other one with a right offset bite plate 103, both of them being provided with tapered holes 101a and 101b.

Figure 7:
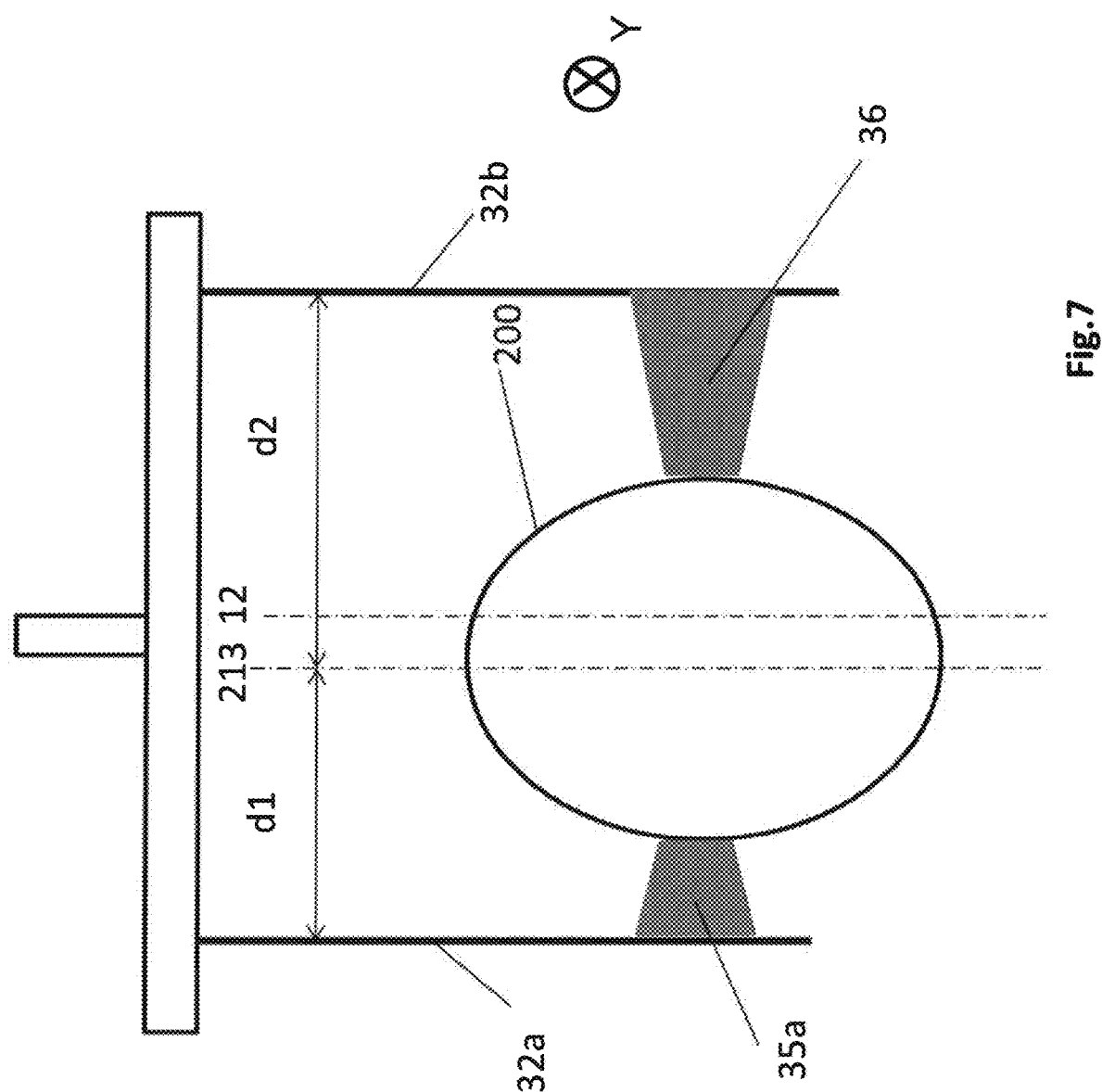
FIG. 7 is a diagram that shows positioning of the patient's head between two temporal holders equipped with temporal contacts of different size according to exemplary embodiments of the application.

To fix the patient's head, the patient positioning unit 30 also comprises a couple of temporal holders 32a and 32b (FIGS. 1 and 7). Each of the temporal holders 32a and 32b is provided with a temporal contact 35a and 35b that contact the temporal of the patient when positioned on the positioning unit 30. The temporal holders 32a and 32b are positioned symmetrically relative to the antero posterior plane 12 of the CBCT imaging device 1. With a standard bite block, the patient's head 200 is also positioned symmetrically relative to the antero-posterior plane 12 and hence contacts 35a and 35b of the same size fit the head of the patient. With the exemplary bite block 100 according to the application with an offset bite plate 102 or 103, the plane of symmetry 213 of the head 200 of the patient, which is also the plane of symmetry of the bite plate 102 or 103, does not coincide with the antero posterior plane 12. The distance d2 between the plane of symmetry 213 of the patient and a first temporal holder 32b is then greater than the distance dl between the plane of symmetry 213 of the head of the patient and a second temporal holder 32a as shown in FIG. 7. Hence, a larger temporal contact 36 must replace the temporal contact 35b to compensate the offset (e.g., between the plane 12 and the plane 113) as shown in FIG. 7. Advantageously, the contacts 35a, 35b and 36 are removable and are for example removably attached (e.g., snapped, attached/detached without tools) to the temporal holders 32a and 32b to change easily the configuration. When a standard bite block is used, then contacts 35a and 35b are used. When left third molars or condyle has to be imaged, a bite block 100 according to the application can be used and mounted on the shafts 32a and 32b in such a way that the bite plate 103 faces the patient and the small contact 35a and the big contact 36 are used. When right third molar or condyle has to be imaged, a bite block 100 according to the application can be used and mounted on the shafts 33a and 33b in such a way that the bite plate 102 faces the patient and the small contact 35b and the large contact 36 are used.

Figure 8:
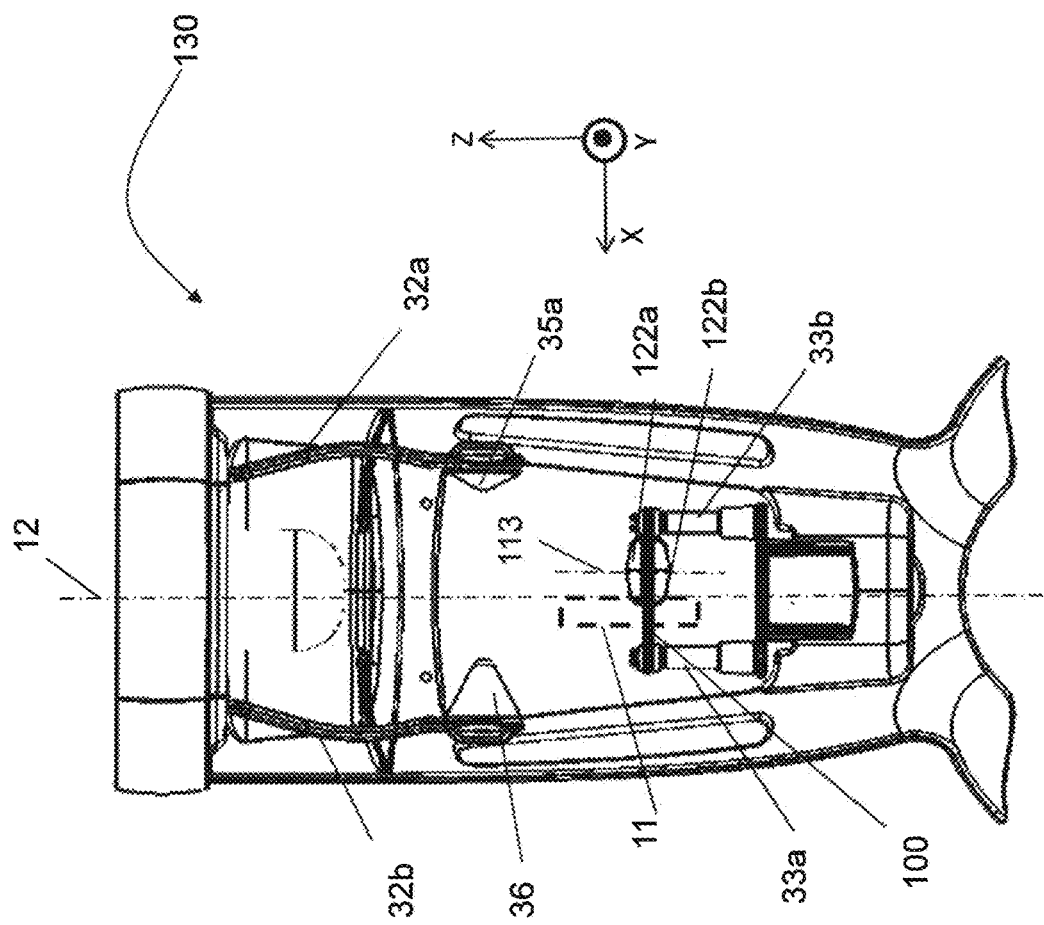
FIG. 8 is a diagram that shows an exemplary patient positioning unit with an exemplary offset bite plate embodiment and exemplary temporal holder embodiments equipped with temporal contacts of different size according to the application.

FIG. 8 represents a patient positioning unit 130 provided with the exemplary bite block 100 positioned on the pair of shafts 33a and 33b. The bite plate 102 is offset relative to the antero posterior vertical plane 12 as it can be distinguished from the position of the upper and the lower flanges 122a and 122b. Actually, the plane of symmetry 113 of the bite plate 102 (which is also the plane of symmetry of the patient's dental arch) is offset from the plane 12. Then, the region of interest 11 is brought closer to the antero posterior plane 12 of the CBCT imaging device 1 and consequently to the rotary axis 5. The x-ray beam can then irradiate the region of interest 11, which in this case is an extremity of the jaw 10, and impinge the active surface of the sensor 7. As the head of the patient is offset relative to the midpoint between the temporal holders 32a and 32b, there is a necessity to position on one temporal holder a contact 36 that is larger than the contact 35b positioned on the other temporal holder.

Figure 9B:
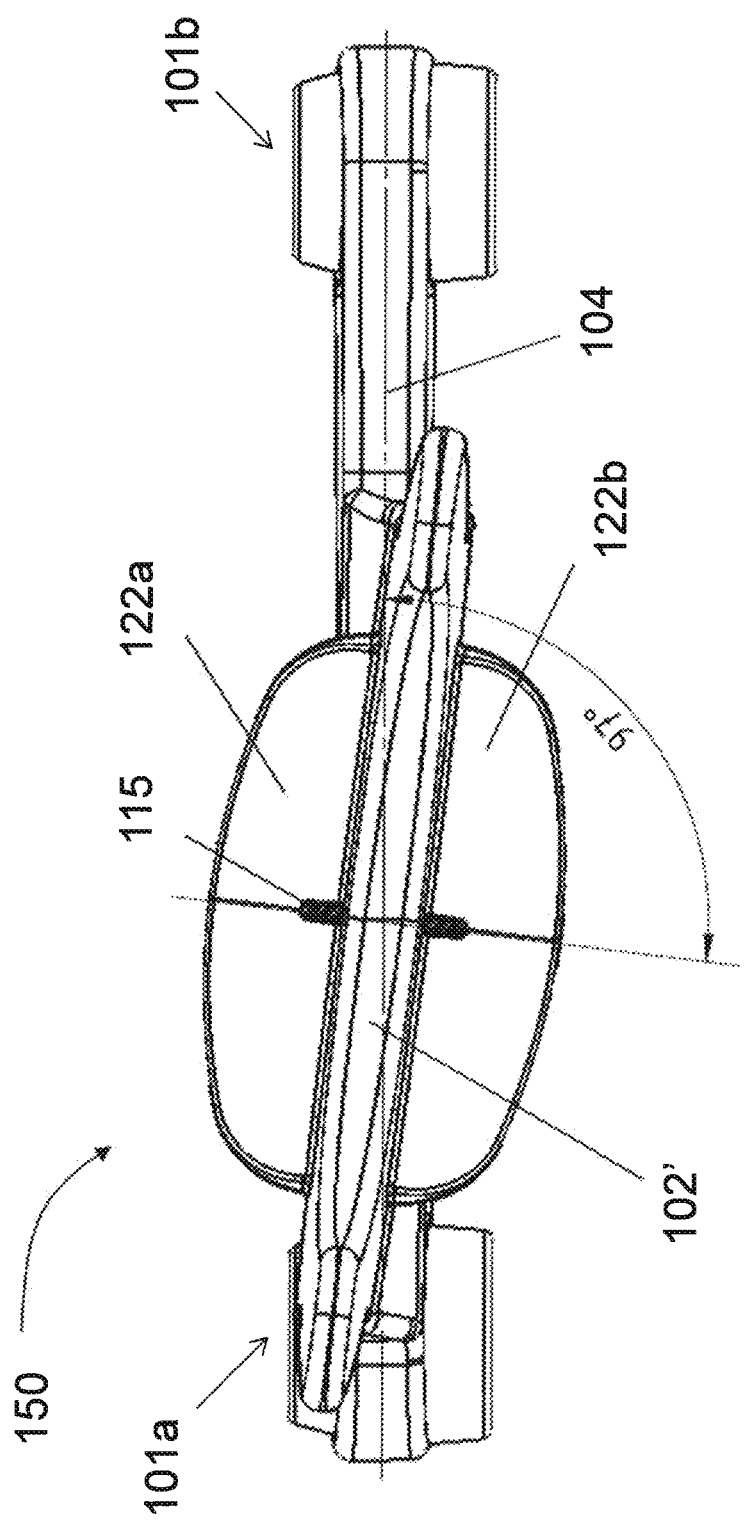
Figure 9C:
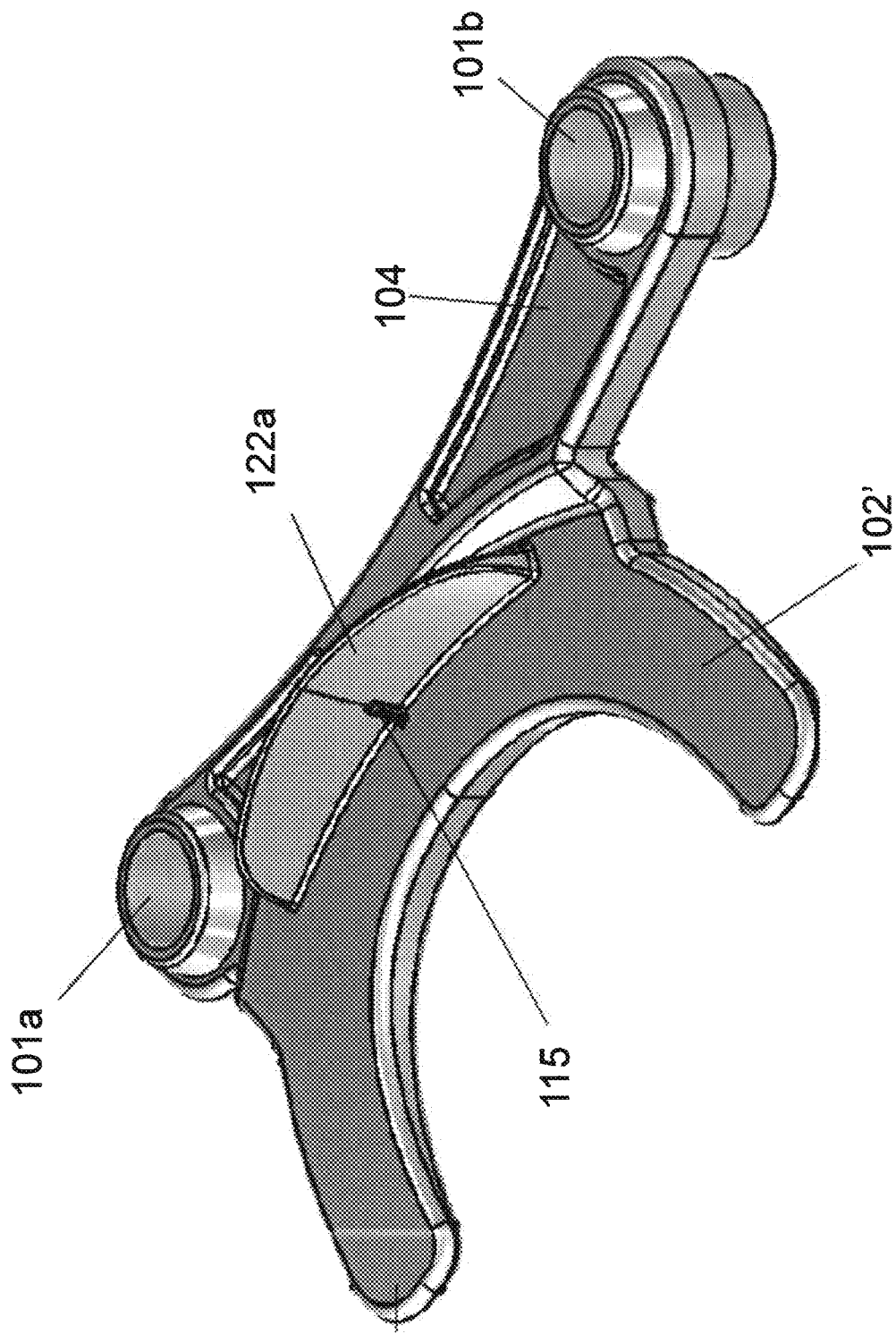
Figure 10:
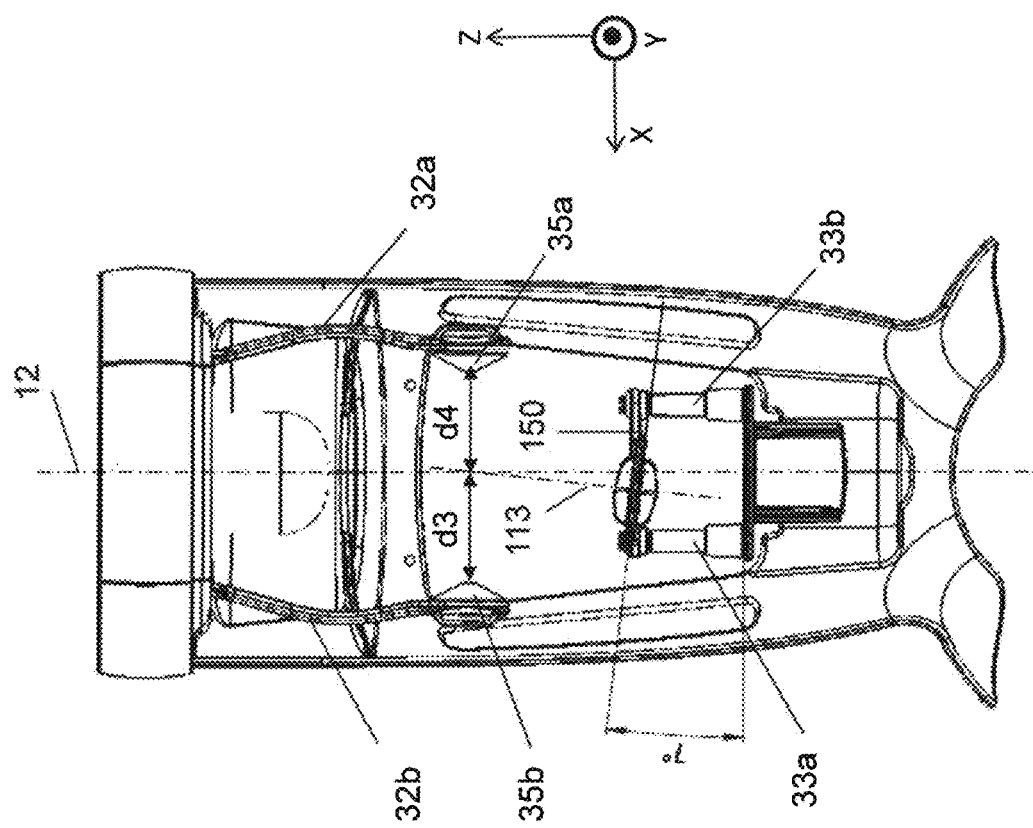
FIG. 10 is a diagram that shows the exemplary bite block embodiment of FIG. 9a-9c and temporal holders equipped with temporal contacts of the same size shown in an exemplary patient positioning unit according to the application.

In an alternative embodiment (FIGS. 9a-9c) a bite plate of an exemplary bite block embodiment 150 can be tilted (e.g., adjustably, fixed) relative to the planar element 104 and to the plane orthogonal to the holes 101a and 101b of the exemplary bite block 150. Again, a bite plate 102' is offset, e.g., the mid-points 115 of the flanges 122a and 122b are offset from the antero posterior plane 12 of the CBCT device. When the patient is positioned on the patient positioning device 130 and bites the bite plate 102', his head is tilted relative to the antero posterior plane 12. Especially, the head is tilted towards the temporal holder that is the most remote from the offset position of the head. With the exemplary bite block embodiment 150 shown in FIGS. 9a-9c, it is not necessary to use a second type of temporal contacts 36. The tilt of the head compensates the offset of the jaw positioning relative to the midline between both temporal holders. It is then possible to image an extremity of the patient's jaw because of the offset of the bite plate 102' while using the same type of temporal contacts 35a and 35b on both temporal holders 32a and 32b, because of the tilt of the bite plate, as illustrated on FIG. 10. The plane of symmetry 113 of the tilted offset bite plate 102' crosses the antero posterior plane 12 at the midpoint between both temporal contacts 35a and 35b. As the distance d3 and d4 are equal, a change of temporal contact is no longer necessary. The tilt angle of the bite plate 102' relative t© the planar element 104 is in the range 3-15°. Preferably, the value of the tilt angle lies in the range 5-10°, though a value of the tilt angle in the range 10-15° can also be contemplated. In a preferred exemplary embodiment, the value of the tilt angle is equal to 7°.

In one exemplary embodiment, exemplary bite block embodiments according to the application can be retrofit and/or used with CBCT imaging device 1.

In one embodiment, a patient positioning structure or a bite piece thereof (e.g., 102, 102', 103) is preferably equipped with a replaceable protective sheath for hygienic reasons. Alternatively, the bite piece can be in the form of a replaceable bite piece, in one embodiment, the patient positioning structure can include a bite wing or a bitable shape or a flat shape corresponding to the dental arch or occlusal surfaces of the upper and/or lower jaw (e.g., solid or elongaeted arms with a gap therebetween). The patient positioning structure is preferably composed of a hard material, particularly a substantially radiolucent material. In one embodiment, patient positioning structure preferably occupies an angular range of a mandibular arch, which is between 20° and 40°, which can substantially reduce or prevents any sideways tipping or tilting of the patient's head. In one embodiment, the patient positioning structure has on its upper surface and on its undersurface a bite groove to accommodate part of the dental arch of the patient's upper and lower jaw respectively. In one embodiment, the patient positioning structure can include sensors to determine when a bite stick is firmly pressed between accusal surfaces of the mandibular and maxillary arches. An audible alert or visual indication can identify the selected tension/force.

Consistent with exemplary embodiments of the application, a computer program utilizes stored instructions that perform on image data that is accessed from an electronic memory. As can be appreciated by those skilled in the image processing arts, a computer program for operating the imaging system in an exemplary embodiment of the present application can be utilized by a suitable, general-purpose computer system, such as a personal computer or workstation. However, many other types of computer systems can be used to execute the computer program of the present application, including an arrangement of networked processors, for example. The computer program for performing exemplary methods/apparatus of the present application may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing exemplary methods/apparatus of the present application may also be stored on computer readable storage medium that is connected to the image processor by way of the internet or other network or communication medium. Those skilled in the art will farther readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used tier storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a type of memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that the computer program product of the present application may make use of various image manipulation algorithms and processes that are well known. It will be further understood that the computer program product embodiment of the present application may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present application, are not specifically shown or described herein and may be selected from such algorithms, systems, hardware, components and elements known in the art.

The invention has been described in detail, and may have been described with particular reference to an exemplary or presently preferred embodiment, but it will be understood that variations and modifications can be effected. For example, exemplary visual indicator embodiments can be detachable (e.g., after alignment and before scanning) in contrast to moving to a retracted position. In one embodiment, a retracted position is a detached position. Also, an exemplary visual indicator embodiments can be mounted to different portions such a nasion with an indicator to then visually align (e.g., by the dentist) to a ear canal and/or an ear rod. Alternatively, exemplary visual indicator embodiments can be electronically detectable as transceivers mounted to alignment mechanisms (e.g., ear rods and a position verification part of a forehead support) that are initially positioned by the dentist relative to the patient, and then can be detected by remote sensors (e.g., transceivers) for confirmation or adjustment of the initial position, displayed (e.g., local at the apparatus or remote at a console), for repeatability and accuracy of this exam or between exams or the like. In one embodiment, a patient support structure can be slidably connected to a chin rest, where the chin rest is connected to the dental imaging apparatus with a prescribed relationship to the movable mount. The presently disclosed exemplary is embodiments are therefore considered in all respects to be illustrative and not restrictive. The scope of the invention is indicated by the appended claims, and all changes that come within the meaning and range of equivalents thereof are intended to be embraced therein.

Exemplary applications of apparatus and/or method embodiments herein were described with respect to imaging of the teeth, however, embodiments of the application are not intended to be so limited, for example additional applications of described embodiments can include but are not limited to medical fields, NDT fields, and/or applications including orthodontics, periodontics, endodontics, prosthodontics, oral and maxillofacial surgery, or pediatric dentistry. Certain exemplary apparatus and/or method embodiments according to the application can be used for dental imaging apparatus including at least one of a panoramic dental imaging apparatus, a combined dental imaging apparatus including a panoramic dental imaging device and at least one of a computed. tomography dental imaging device image, a cephalometric dental imaging device, an ultrasonic dental imaging device, or an ENT a radiographic imaging device.

Exemplary embodiments according to the application can include various features described herein (individually or in combination).

While the invention has been illustrated with respect to one or more implementations, alterations and/or modifications can be made to the illustrated examples without departing from the scope of the appended claims. In addition, while a particular feature of the invention can have been disclosed with respect to one of several implementations, such feature can be combined with one or more other features of the other implementations as can be desired and advantageous for any given or particular function. The term "at least one" or is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a scope of the invention being indicated by the following claims, and all changes that come within the meaning and range of equivalents thereof are intended to be embraced therein.

The invention claimed is:

1. A dental imaging apparatus, comprising:
a movable mount comprising at least a radiation source and a digital imaging sensor, the movable mount being adjustable to compensate for a patient's height;
an actuator that is energizable to move the movable mount in a scan pattern about an imaging area;
a computer in signal communication with the digital imaging sensor and configured to acquire one or more of two-dimensional images of the imaging area from the digital imaging sensor positioned relative to the radiation source for the scan pattern;
a patient positioning unit coupled to the movable mount and having a first spatial relationship to the scan pattern, where in the first spatial relationship an antero-posterior plane and a plane of symmetry of a dental arch of a patient are coplanar; and
where the patient positioning unit is configured for movement with the movable mount to compensate for the patient's height and comprises a bite block configured to provide a second spatial relationship to the scan pattern, where in the second spatial relationship the antero-posterior plane and the plane of symmetry of the dental arch of the patient are not coplanar; and
where the antero-posterior plane is a vertical plane centered on the patient positioning unit, and where the plane of symmetry of the dental arch of the patient is a plane centered on the patient's dental arch.

2. The dental imaging apparatus of claim 1, where the antero-posterior plane is oriented in a front-to-rear direction of the patient when the patient is positioned on the patient positioning unit.

3. The dental imaging apparatus of claim 1, where the bite block comprises a dental bite plate, where in the second spatial relationship the dental bite plate is configured to be held between a patient's teeth relative to the antero-posterior plane, where a plane of symmetry of the dental bite plate is spaced apart and offset from the antero-posterior plane.

4. The dental imaging apparatus of claim 1, where the bite block comprises:

a planar element comprising at least one fastener, where the bite block is removably fastened by the at least one fastener to the movable mount; and at least one bite plate can be coupled to the planar element at a longitudinal side, where the at least one bite plate is offset relative to the antero-posterior plane.

5. The dental imaging apparatus of claim 4, where the bite block is one single piece that can be positioned relative to the movable mount using the at least one fastener.

6. The dental imaging apparatus of claim 4, where the at least one bite plate is tilted relative to the planar element, which is substantially horizontal when fastened by the at least one fastener.

7. The dental imaging apparatus of claim 4, where the at least one bite plate is adjustably tilted relative to the planar element.

8. The dental imaging apparatus of claim 4, where the patient positioning unit further comprises two temporal holders, where a plane of symmetry of the at least one bite plate is offset relative to the antero-posterior plane or offset relative to the two temporal holders.

9. The dental imaging apparatus of claim 8, where the two temporal holders comprise temporal contacts, and where the temporal contacts are asymmetrical in size.

10. The dental imaging apparatus of claim 1, where the bite block comprises at least one surface to determine an occlusal plane in the imaging area.

11. The dental imaging apparatus of claim 1, where the dental imaging apparatus is at least one of a panoramic dental imaging apparatus, a combined dental imaging apparatus including a panoramic dental imaging device and at least one of a computed tomography dental imaging device, a cephalometric dental imaging device, an ultrasonic dental imaging device, or an ENT radiographic imaging device.

12. The dental imaging apparatus of claim 1, where the patient positioning unit further comprises a chin rest, where the bite block is slidably connected to the chin rest, where the chin rest is connected with a prescribed relationship to the movable mount.

13. A method of positioning a subject for dental radiographic imaging, the method comprising:

providing a patient positioning unit oriented to an imaging area of a dental imaging apparatus;

providing a bite block including opposing surfaces to provide a prescribed spatial relationship, where the bite block comprises at least one bite plate having a plane of symmetry and a shape corresponding to a dental arch, where the prescribed spatial relationship offsets an antero-posterior plane of the patient positioning unit and the plane of symmetry of the at least one bite plate, and mounting the bite block to the patient positioning unit to provide the prescribed spatial relationship.

14. The method of claim 13, further comprising:

attaching the bite block by at least one fastener to the patient positioning unit, where the bite block comprises a planar element; and providing the at least one bite plate in the bite block positioned along a longitudinal side of the planar element, where the at least one bite plate is offset relative to two temporal holders of the patient positioning unit.

15. The method of claim 13, where the at least one bite plate is tilted relative to a horizontal plane when the bite block is fastened by at least one fastener to the patient positioning unit, where dental radiographic imaging is dental panoramic imaging.

16. The method of claim 13, where the bite block is mounted to the patient positioning unit in at least two stationary positions.

* * * * *